United States Patent [19]

Chodnekar et al.

[11] 3,946,040
[45] Mar. 23, 1976

[54] PROPYNYL BENZYL ETHERS

[75] Inventors: Madhukar Subraya Chodnekar, Basel; Albert Pfiffner, Pfaffhausen; Norbert Rigassi, Arlesheim; Ulrich Schwieter, Reinach; Milos Suchy, Pfaffhausen, all of Switzerland

[73] Assignee: Hoffmann-La Roche Inc., Nutley, N.J.

[22] Filed: Dec. 26, 1973

[21] Appl. No.: 428,291

Related U.S. Application Data

[62] Division of Ser. No. 235,037, March 15, 1972, Pat. No. 3,840,604.

[52] U.S. Cl............................ 260/340.3; 260/340.5
[51] Int. Cl.². .............. C07D 317/54; C07D 319/18
[58] Field of Search........................ 260/340.3, 340.5

[56] References Cited
UNITED STATES PATENTS

| | | | |
|---|---|---|---|
| 2,421,569 | 6/1947 | La Forge et al. | 260/340.5 |
| 3,338,950 | 8/1967 | Seki et al. | 260/465 |
| 3,423,428 | 1/1969 | Fellig et al. | 260/340.5 |
| 3,686,222 | 8/1972 | Chodnekar et al. | 260/340.5 |
| 3,796,726 | 3/1974 | Edwards | 260/340.5 |
| 3,839,562 | 10/1974 | Chodnekar et al. | 260/340.3 X |

FOREIGN PATENTS OR APPLICATIONS

| | | | |
|---|---|---|---|
| 2,115,673 | 3/1971 | Germany | 260/340.3 |
| 46-5,699 | 2/1971 | Japan | 260/340.5 |

*Primary Examiner*—Lorraine A. Weinberger
*Assistant Examiner*—Michael Shippen
*Attorney, Agent, or Firm*—Samuel L. Welt; Jon S. Saxe; Richard A. Gaither

[57] ABSTRACT

Propynyl benzyl ethers having juvenile hormone-like activity which are 4-halogen, lower alkyl, lower alkoxy or propynyloxy substituted or 3,4-lower alkylenedioxy substituted and which can also be 3,5- and/or α-substituted, and insecticide compositions that include at least one propynyl benzyl ether and that can also include a conventional insect-poison.

4 Claims, No Drawings

PROPYNYL BENZYL ETHERS

This is a division of application Ser. No. 235,037, filed Mar. 15, 1972, now U.S. Pat. No. 3,840,604, entitled "Propynl Benzyl Ethers."

BACKGROUND OF THE INVENTION

Many conventional insect-poisons, such as the carbamates, the pyrethrins and the chlorinated hydrocarbons, although highly lethal to numerous insects, cannot be used indiscriminately. Despite their value for protecting foodstuffs, feeds, textiles and plants, these insect-poisons tend to remain indefinitely in the environment after being used. They are not naturally degraded, and by remaining undegraded in the environment, their lingering residues tend to find their way into foods intended for human or cattle consumption. Moreover, because apparently many of these insect-poisons are not quantitatively degraded by mammalian organisms, their use can lead to the indirect injury of humans or other mammals. Thus, the decision to use many conventional insect-poisons cannot be made without some significant reservations. There has been a need, therefore, for effective insect-poison compositions having a reduced tendency to linger in the environment, to contaminate food and to resist degradation in mammals.

SUMMARY OF THE INVENTION

In accordance with this invention, it has been found that propynyl benzyl ethers of the formula:

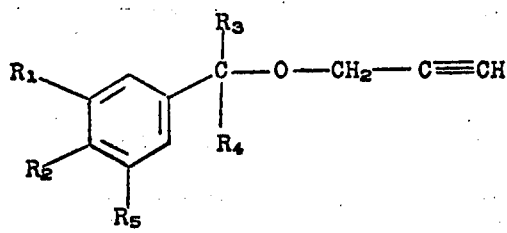   I wherein $R_1$ is individually hydrogen, halogen, lower alkyl, lower alkoxy or propynyloxy and $R_2$ is individually halogen, lower alkyl, lower alkoxy or propynyloxy or $R_1$ and $R_2$ taken together form a lower alkylenedioxy group; $R_3$ and $R_4$ are hydrogen or lower alkyl; and $R_5$ is hydrogen or lower alkoxy; are useful in killing and preventing the proliferation of insects by upsetting their hormonal balance.

In accordance with another embodiment of this invention, insecticide compositions are provided which include at least one of the propynyl benzyl ethers and which can also include a conventional insect-poison.

The propynyl benzyl ethers of formula I are prepared by reacting an alcohol of the formula:

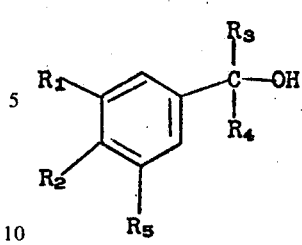   II wherein $R_1$, $R_2$, $R_3$, $R_4$ and $R_5$ are as above; with a halide of the formula:

$$CH{\equiv}C-CH_2-X \qquad III$$

wherein X is chlorine, bromine or iodine.

DETAILED DESCRIPTION OF THE INVENTION

As used throughout this application, the term "insect-poison" comprehends a compound or a combination of compounds which kill, disable or repel insects by either their chemical or physical effects upon the insects systems. In the insecticide compositions of this invention, any conventional insect-poison can be utilized. Among the preferred insect-poisons are the carbamates, pyrethrins, chlorinated hydrocarbons, phosphoric acid esters, and thio-phosphoric acid esters. Among the carbamates, especially preferred are the following:

1-naphthyl-methylcarbamate (Sevin);
m-(1-methylbutyl)-phenyl methylcarbamate;
m-(1-ethyl-propyl)-phenyl methylcarbamate;
3-methyl-5-isopropyl-phenyl methylcarbamate;
m-{[(dimethylamino)-methylene]-amino}-phenyl methylcarbamate; and
1-dimethylcarbamoyl-5-methyl-3-pyrazolyl dimethylcarbamate Among the pyrethrins, especially preferred are the following:

pyrethrum, particularly pyrethrin I and II, cinerin I and II, and jasmolin II;
2,2-dimethyl-3-(2-methylpropenyl)-cyclopropanecarboxylic acid 1-cyclohexene-1,2-dicarboximidomethyl ester;
2,2-dimethyl-3-(2-methylpropenyl)-cyclopropanecarboxylic acid 5-benzyl-3-furyl-methyl ester; and
2-allyl-4-hydroxy-3-methyl-2-cyclopenten-1-one esterified with a mixture of cis and trans 2,2-dimethyl-3-(2-methylpropenyl)-cyclopropanecarboxylic acid (Allethrin).

Among the halogenated hydrocarbons, especially preferred are the following:

1,2,3,4,10,10-hexachloro-1,4,4a,5,8,8a-hexahydro-1,4-endo-exo-5,8-dimethano-naphthalene;
octachloro-camphor;
1,1,1-trichloro-2,2-bis(p-chlorophenyl)-ethane;
1,2,3,4,10,10-hexachloro-6,7-epoxy-1,4,4a,5,6,7,8,8a-octahydro-1,4-endo-endo-5,8-dimethano-naphthalene;
1,2,3,5,6,7,8,8-octachloro-2,3,3a,4,7,7a-hexahydro-4,7-methano-indene;

1,4,5,6,7,8,8-heptachloro-3a,4,7,7a-tetrahydro-4,7-endomethano-indene;
1,1,1-trichloro-2,2,bis-(p-methoxyphenyl)-ethane (Methoxychlor);
hexachloro-cyclohexane;
1,2,3,4,10,10-hexachloro-6,7-epoxy-1,4,4a,5,6,7,8,8a-octahydro-1,4-endo-exo-5,8-dimethano-naphthalene;
1,1,1-trichloro-2,2-bis(p-chlorophenyl)-ethanol (Kelthane);
1,1-dichloro-2,2-bis(p-ethylphenyl)-ethane;
1,1-dichloro-2,2-bis-(p-chlorophenyl)-ethane; 1,2-
1,2-dibromo-3-chloro-propane;
1,2-dibromo-ethane; and
methyl bromide.

Among the phosphoric acid esters, especially preferred are the following:
2-carbomethoxy-1-prop-2-enyl dimethyl phosphate;
1,2-dibromo-2,2-dichloroethyl dimethyl phosphate;
1-chloro-diethylcarbamoyl-1-prop-2-enyl dimethyl phosphate;
tetraethyl pyrophosphate;
tetra-N-propyl dithiono-pyrophosphate;
0,0-dimethyl-0-2,2-dichlorovinyl-phosphate;
0,0-dimethyl-0-[1-methyl-2-(1-phenyl-carbethoxy)-vinyl]-phosphate; and
0,0-dimethyl-(1-hydroxy-2,2,2-trichloroethyl)-phosphonate.

Among the thiophosphoric acid esters, especially preferred are the following:
S-[1,2-bis-(carbethoxy)-ethyl]-0,0-dimethyl-dithiophosphate (Malathion);
0,0-diethyl-0-(2-isopropyl-4-methyl-6-pyrimidyl)-thiophosphate;
0,0-dimethyl-0-(p-nitrophenyl)-thiophosphate;
0,0-diethyl-0-(p-nitrophenyl)-thiophosphate;
0,0-dimethyl-S-[4-oxo-2,2,3-benzotriazin-3-(4H)-yl-methyl]-dithiophosphate;
0,0-diethyl-S-(2-ethylthio)-ethyl-dithiophosphate;
0,0-dimethyl-S-(2-ethylthio)-ethyl-thiophosphate;
0,0-dimethyl-0-(2-ethylthio)-ethyl-thiophosphate.
0,0-diethyl-S-(2,5-dichlorophenyl-thiomethyl)-dithiophosphate;
0,0-dimethyl-S-(N-methylcarbamoyl-methyl)-dithiophosphate;
2,3-p-dioxandithio S,S'-bis-(0,0-diethyl-dithiophosphate);
0,0,0',0'-tetraethyl-S,S'-methylene-bis-(dithiophosphate); and
S-{[p-chlorophenyl)-thio]-methyl}-0,0-diethyl-dithiophosphate.

Among other preferred insect-poisons, especially preferred are the following:
N,N-dimethyl-N'-(2-methyl-4-chlorophenyl)-formamidine;
2-(p-tert.butylphenoxy)-isopropyl 2-chloroethyl sulphite;
p-chlorophenyl 2,4,5-trichlorophenyl sulphone;
6,7,8,9,10,10-hexachloro-1,5,5a,6,9,9a-hexahydro-6,9-methano-2,4,3-benzodioxathiepine 3-oxide;
N-(1,1,2,2-tetrachloroethyl-sulphinyl)-cyclohex-4-ene-1,2-dicarboximide;
2-dodecanoic acid 2-thiocyanato-ethyl ester;
crotonic acid 2-(1-methyl-heptyl)-4,6-dinitro-phenyl ester;
N-trichloro-methylthio-cyclohex-4-ene-1,2-dicarboximide;
N-trichloro-methylthio-phthalimide;
3,4-methylenedioxy-6-propyl-benzyl butyl diethylene glycol ether; and
rotenone.

As also used throughout this application, the term "propynyl benzyl ether" comprehends a propynyl benzyl ether of formula I which has juvenile hormone-like activity. The juvenile hormone-like activity of the propynyl benzyl ethers interferes with insects' hormonal systems, causing their transformation to the imago, their laying of viable eggs and the development of their eggs to be disrupted. These disruptions, which are the characteristics of juvenile hormone activity, effectively prevent affected insects from maturing and proliferating.

Among the preferred propynyl benzyl ethers are the compounds of the formula:

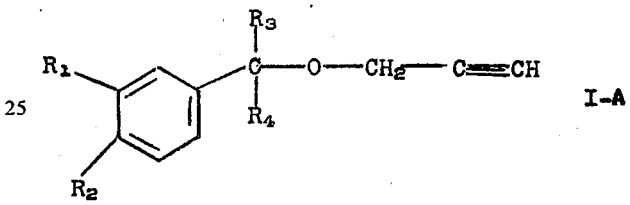

wherein $R_1$, $R_2$, $R_3$ and $R_4$ are as above.
Especially preferred are the compounds:
6-[(2-propynyloxy)methyl]-1,4-benzodioxan;
3,4-dihydro-7-[(2-propynyloxy)methyl]-2H-1,5-benzodioxepin;
3,4-methylenedioxy-α-(2-propynyloxy)-toluene;
3,4-dimethoxy-α-(2-propynyloxy)-toluene;
3,4-dihydro-7-[1-(2-propynyloxy)propyl]-2H-1,5-benzodioxepin;
6-[1-(2-propynyloxy)propyl]-1,4-benzodioxan;
1,2-methylenedioxy-4-[1-(2-propynyloxy)propyl]-benzene; and
diethylpiperonyl propargyl ether;
particularly 3,4-dimethoxy-α-(2-propynyloxy)toluene.

As further used throughout this application, the term "lower alkyl" comprehends straight chain and branched chain saturated aliphatic groups having 1 to 6 carbon atoms, preferably methyl or ethyl. As used herein, the term "lower alkoxy" comprehends alkoxy groups having 1 to 6 carbon atoms, preferably methoxy and ethoxy. As also used herein, the term "lower alkylenedioxy" comprehends alkylenedioxy groups containing 1 to 4 carbon atoms, preferably 1 to 3 carbon atoms, particularly methylenedioxy and ethylenedioxy. As further used herein, the term "halogen" or "halo" comprehends all four halogens, fluorine, chlorine, bromine and iodine, unless otherwise stated.

The propynyl benzyl ethers of formula I are useful in the control of invertebrate animals, such as arthropods and nematodes, especially against various kinds of insects. For example, they are active against Diptera such as house flies, fruit flies (*Drosophila melanogaster*), midges and stable flies, Lepidoptera such as cabbage looper (*Trichoplusia ni*), bud moth, lazy bombyx, owlet moth and owlet caterpillar, and Coleoptera such as alfalfa weevils (*Hypera postica*), confused flour beetles (*Tribolium confusum*), aphids, Colorado beetles, spider-mites and Prodenia litura.

The propynyl benzyl ethers are also practically non-toxic to vertebrates. The toxicity of the compounds is greater than 1,000 mg/kg body weight. Moreover, these compounds are readily degraded and the risk of accumulation is therefore excluded. Therefore, these compounds can be used without fear or danger in the control of pests in animals, plants, foods, and textiles.

Generally, in controlling invertebrate animals, the propynyl benzyl ethers are applied to the material to be protected, e.g., foodstuffs, feeds, textiles and plants, in concentrations of from about $10^{-3}$ to $10^{-6}$ gm/cm$^2$ of the material to be protected. Generally, it is preferred to utilize the propynyl benzyl ethers in a composition with a suitable inert carrier. Any conventional inert carrier can be utilized.

The propynyl benzyl ethers can, for example, be used in the form of emulsions, suspensions, dusting agents, solutions or aerosols. In special cases, the materials to be protected can also be directly impregnated with the appropriate compound or with a solution thereof. Moreover, the compounds can also be used in a form which only releases them by the action of external influences (e.g., contact with moisture) or in the animal body itself.

The propynyl benzyl ethers can be used as solutions suitable for spraying on the material to be protected. Such solutions should contain the ether in a concentration of 0.01% by weight to 0.5% by weight, preferably 0.1% by weight. These solutions can be prepared by dissolving or dispersing these compounds in a solvent, such as mineral oil fractions, cold tar oils, oils of vegetable or animal origins, hydrocarbons such as napthalenes, ketones such as methyl ethyl ketone, and chlorinated hydrocarbons such as tetrachloroethylene and tetrachlorobenzene. These compounds can also be provided in forms suitable for dilution with water to form aqueous liquids such as, for example, emulsion concentrates, pastes or powders. The propynyl benzyl ethers above can be combined with solid carriers for making, dusting or strewing powders such as, talc, kaolin, bentonite, calcium carbonate, and calcium phosphate. The compositions containing the compounds of formula I above can also contain, if desired, emulsifiers, dispersing agents, wetting agents, and/or other active substances such as fungicides, bactericides, nematocides, fertilizers and the like. The materials which are to be protected act as bait for the insect. In this manner, the insect, by contacting the material impregnated with the propynyl benzyl ether, also contacts the ether itself.

In addition, it has been surprisingly found that the activity of a conventional insect-poison can be increased by a factor of about 2 to 10 and more by combining the insect-poison with a propynyl benzyl ether. The propynyl benzyl ether and the insect-poison, when combined in an insecticide composition, provide up to the same degree of insecticidal activity with 10%–50% of the previously used amounts of insect-poison, thereby reducing the residue of insect-poison in the environment to a tolerable degree. Such a composition possesses an additional advantage, i.e., after the abatement of the insecticidal action of the insect-poison, the juvenile hormone action comes to the fore so that the sequence of generations is interrupted and the pests are indirectly killed.

Thus, the rapidly commencing action of the insect-poisons can be synergistically augmented by the juvenile hormone action of the propynyl benzyl ethers, which disturbs the subsequent re-building of the insect population, thereby permitting the intervals between sprayings of the insecticide composition to be extended.

The proportions of the two components of the combined insecticide composition, in accordance with this invention, can vary within wide limits according to the purpose of use, the mode of application, the pests to be controlled and other factors. Any ratio of the insect-poison and propynyl benzyl ether can be utilized as the active substance. However, it is preferred to use approximately 1 to 10 parts by weight of a propynyl benzyl ether and approximately 1 to 10 parts by weight of an insect-poison, with about equal parts by weight of the two components being especially preferred.

Pest-control agents containing the combined insecticide composition in accordance with this invention can be prepared in the form of granulates, concentrates or ready-to-use pest-control agents. The concentration of the insecticide composition depends upon the form of pest-control agent and the mode of use. The pest-control agents in accordance with this invention can contain solid or liquid carrier material to form solutions, sprays, aerosols or dusting powders, as set forth above with respect to the use of the propynyl benzyl ether with an inert carrier material.

In general, the pest-control agents utilizing the combined insecticide compositions of the present invention can be prepared according to a process such as is described, for example, in *Farm Chemicals*, Vol. 128, pages 52 ff. The pest-control agents in accordance with this invention can additionally utilize yet other additives such as emulsifiers or masking agents.

The pest-control agents in accordance with this invention can exist in the form of concentrates which are suitable for storage and transport. Such concentrates can, for example, contain 40–80% by weight of the synergistically active combination of insect-poison and propynyl benzyl ether as the active substance and 60–20% by weight of an inert carrier material. In preparing these concentrates, any conventional, liquid, or solid inert carrier material can be utilized. Among the inert carrier materials which can be utilized are the liquid solvents and solid materials mentioned above.

These concentrates can be further diluted with similar or different carrier materials to concentrations which are suitable for practical use as ready-to-use pest-control agents. In the ready-to-use agents, the active substance concentration is preferably 0.1–20 weight percent of the synergistically active substance and 99.9–80 weight percent of an inert carrier material, with 0.1–10 weight percent of the active substance and 99.9–90 weight percent of the inert carrier being especially preferred. The active substance concentration can also be smaller or larger than the preferred concentration. In preparing these ready-to-use pest-control agents, any conventional liquid or solid inert carrier material may be utilized. Among the inert carrier materials which may be utilized are the liquid and solid materials mentioned above.

The reaction of an alcohol of formula II with a halide of formula III, preferably a bromide, can be carried out in the presence of a base such as an alkali metal, an alkali metal amide or an alkali metal hydride. The preferred bases are the alkali metal hydrides, particularly sodium hydride. This reaction can be carried out in an inert organic solvent. In this reaction, any conventional, inert organic solvent can be utilized. Preferred solvents include dimethylformamide, dioxane and hexamethylphosphoric acid triamide. In this reaction, temperature and pressure are not critical, and the reaction can be carried out at room temperature (22°C.) and atmospheric pressure. Preferably the reaction is carried out at a temperature of −20°C. to the reflux temperature of the reaction mixture, with about room temperature being particularly preferred.

The alcohol starting materials of formula II can be prepared in a simple and known manner either by reacting an aldehyde or ketone of the formula:

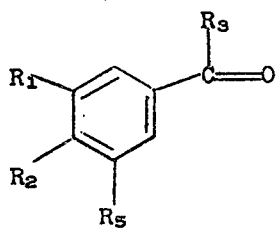

IV wherein $R_1$, $R_2$, $R_3$ and $R_5$ are as above;
with a Grignard compound of the formula:

$$R'_4-MgBr \qquad V$$

wherein $R'_4$ is lower alkyl; or by reducing an aldehyde or ketone of formula IV with a complex metal hydride.

The compound of formul IV is conveniently reacted with the Grignard, lower alkyl magnesium halide of formula V under conventional conditions of temperature, pressure and absence of moisture. The Grignard product, which results, can be subsequently decomposed with ice-water in a conventional manner to yield the alcohol of formula II.

The examples which follow illustrate the invention. All temperatures are in degrees Centigrade. Room temperature is about 22°C. Unless otherwise stated, the ether solvent utilized is diethyl ether. The low-boiling petroluem ether utilized has a boiling point of 30° to 45°C.

EXAMPLE 1

A solution of 16.6 g of 1,4-benzodioxan-6-methanol in 20 ml of dimethylformamide is added dropwise with stirring to a suspension of 12.5 g of sodium hydride in 75 ml of dimethylformamide. 11.8 g of propargyl bromide are then added dropwise. The mixture is stirred for 3 hours at room temperature, cooled in an ice-bath, decomposed with 20 ml of ice-water, diluted with 150 ml of water and extracted three times with 150 ml of diethyl ether each time. The ether extract is washed with water, dried over sodium sulphate and evaporated. The oily residue is chromatographed on silica gel using benzene as the elution agent. There is obtained 6-[(2-propynyloxy)methyl]-1,4-benzodioxan; $n_D^{24} = 1.5487$.

EXAMPLE 2

Utilizing the procedure of Example 1, 1,3-benzodioxepine-7-methanol is converted to 3,4-dihydro-7-[(2-propynyloxy)methyl]-2H-1,5-benzodioxepine; $n_D^{24} = 1.5811$.

EXAMPLE 3

Utilizing the procedure of Example 1, piperonyl alcohol is converted to 3,4-methylenedioxy-α-(2-propynyloxy)-toluene; $n_D^{24} = 1.5409$.

EXAMPLE 4

Utilizing the procedure of Example 1, veratryl alcohol is converted to 3,4-dimethoxy-α-(2-propynyloxy)-toluene; $n_D^{24} = 1.5389$.

EXAMPLE 5

A solution of 20.8 g of α-ethylveratryl alcohol in 15 ml of dimethylformamide is added dropwise with stirring to a suspension of 12.5 g of sodium hydride in 75 ml of dimethylformamide. The mixture is stirred for 0.5 hour at room temperature (about 22°C.), and 11.8 g of propargyl bromide are then added dropwise, the temperature not being allowed to exceed 30°C. After stirring for 3 hours at room temperature, the mixture is cooled in a ice-bath to 5°C., decomposed with ice-cold water at a temperature of approximately 15°C. and extracted three times with 150 ml of diethyl ether. The extract is washed neutral with water, dried over sodium sulphate, filtered and the filtrate evaporated to dryness under reduced pressure. The oily residue is chromatographed on silica gel using benzene/ether (9:1 parts by volume) as the elution agent. There is obtained 1,2-dimethoxy-4-[1-(2-propynyloxy)propyl]-benzene; $n_D^{24} = 1.5248$.

EXAMPLE 6

Utilizing the procedure of Example 5, α-ethyl-3,4-dihydro-2H-1,5-benzodioxepine-7-methanol is converted to 3,4-dihydro-7-[1-(2-propynyloxy)propyl]-2H-1,5-benzodioxepin; $n_D^{24} = 1.5304$.

EXAMPLE 7

Utilizing the procedure of Example 5, α-ethyl-1,4-benzodioxan-6-methanol is converted to 6-[1-(2-propynyloxy)-propyl]-1,4-benzodioxan; $n_D^{24} = 1.5336$.

EXAMPLE 8

Utilizing the procedure of Example 5, α-ethylpiperonyl alcohol is converted to 1,2-methylenedioxy-4-[1-(2-propynyloxy)propyl]-benzene; $n_D^{24} = 1.5256$.

EXAMPLE 9

38.4 g of 3,4-dimethoxybenzyl-α-ethynyl alcohol are dissolved in 200 ml of ethyl acetate and hydrogenated in the presence of 1 g of Adams catalyst until no more hydrogen is taken up by the mixture. After completion of the hydrogenation, the catalyst is filtered off and the solvent completely evaporated. There remains behind α-ethylveratryl alcohol; b.p. = 114°-115°C/0.5 mmHg.

EXAMPLE 10

Utilizing the procedure of Example 9, α-ethynylpiperonyl alcohol is converted to α-ethylpiperonyl alcohol; b.p. = 101°C/0.6 mmHg.

EXAMPLE 11

Utilizing the procedure of Example 9, α-ethynyl-1,4-benzodioxan-6-methanol is converted to α-ethyl-1,4-benzodioxan-6-methanol; b.p. = 108°C/0.02 mmHg.

EXAMPLE 12

Utilizing the procedure of Example 9, α-ethynyl-3,4-dihydro-2H-1,5-benzodioxepine-7-methanol is converted to α-ethyl-3,4-dihydro-2H-1,5-benzodioxepine-7-methanol; b.p. = 115°–116°C/0.01 mmHg.

EXAMPLE 13

A solution of 5 g of α, α-diethylpiperonyl alcohol in 10 ml of tetrahydrofuran is added dropwise with stirring to a suspension of 2.5 g of sodium hydride in 25 ml of tetrahydrofuran. The mixture is then stirred for 1 hour at room temperature and thereafter treated dropwise with 6 g of propargyl bromide, the temperature being held below 30°C. The mixture is cooled in an ice-bath, decomposed with ice-cold water and extracted with diethyl ether. The extract is washed neutral with water, dried over sodium sulphate, filtered and the filtrate evaporated to dryness. After chromatography on silica gel and elution with benzene, there is obtained α, α-diethylpiperonyl propargyl ether; $n_D^{24}$ = 1.5291.

EXAMPLE 14

7.6 g of 3′, 4′-methylenedioxy-propiophenone are dissolved in 40 ml of absolute diethyl ether and added under a nitrogen atmosphere to a Grignard solution prepared from 1.2 g of magnesium and 5.4 g of ethyl bromide in 15 ml of absolute diethyl ether. The mixture is heated at reflux for 1.5 hours and then stirred at room temperature. The mixture is cooled in an ice-bath and decomposed by the addition of ice-water. A concentrated aqueous solution of ammonium chloride is then added, and the solution extracted twice with 500 ml of diethyl ether each time. The combined ether extracts are washed neutral with water, dried over sodium sulphate and evaporated to dryness. The residual oil is distilled and there is obtained colorless, α, α-diethylpiperonyl alcohol; b.p. = 106°–107°C/0.65 mmHg.

EXAMPLE 15

15 g of a 50% (by weight) dispersion of sodium hydride in oil are washed free from oil with three portions of low-boiling petroleum ether and then added to 100 ml of dimethylformamide. 19.8 g of 3,4,5-trimethoxybenzyl alcohol are slowly added dropwise to the resulting mixture. The mixture thus obtained is stirred for 1 hour, and 18 g of propargyl bromide are then added dropwise thereto. The mixture is stirred for 1 hour, and the excess sodium hydride is decomposed by treatment with 200 ml of water. The mixture is extracted with 300 ml of diethyl ether, the ether extract is washed neutral, dried over sodium sulphate and evaporated. The residue is chromatographed on silica gel with benzene/ether (3:1 parts by volume). There is obtained 3,4,5-trimethoxy-α-(2-propynyloxy)-toluene which is distilled at 0.2 mmHg; b.p. = 115°C.

EXAMPLE 16

25 g of a 50% (by weight) dispersion of sodium hydride in oil are washed free from oil with three portions of low-boiling petroleum ether and then added to 75 ml of dimethylformamide. 13.8 g of p-methoxybenzyl alcohol are added dropwise to the resulting mixture over a period of 1 hour with stirring. After 1 hour, 11.8 g of propargyl bromide are added with stirring at such a rate that the temperature does not exceed 35°–40°C. The mixture is stirred at room temperature for a further 3 hours, then cooled in an ice-bath to 0°–5°C., and the excess sodium hydride decomposed with ice-water. After the addition of a further 100 ml of water, the mixture is extracted three times with diethyl ether, the ether extract washed neutral with water, dried over sodium sulphate and evaporated. The residue is chromatographed on silica gel using methylene chloride as the elution agent. There is obtained p-methoxy-α-(2-propynyloxy)-toluene; $n_D^{24}$ = 1.5273.

EXAMPLE 17

25 g of a 50% (by weight) dispersion of sodium hydride in oil are washed free from oil with three portions of low-boiling petroleum ether and then added to 75 ml of absolute dimethylformamide. 14.2 g of p-chlorobenzyl alcohol are added portionwise to the resulting mixture with stirring over a period of 1 hour, and then 11.8 g of propargyl bromide are added so that the temperature does not exceed 35°–40°C. The mixture is stirred for a further 3 hours at room temperature and then cooled in an ice-bath to 0°–5°C. Water is cautiously added in order to decompose the excess sodium hydride. After the addition of a further 100 ml of water, the mixture is extracted with diethyl ether, the ether extract washed neutral with three portions of water, dried over sodium sulphate and evaporated. The residue is chromatographed on silica gel using methylene chloride as the elution agent. There is obtained p-chlorobenzyl 2-propynyl ether; $n_D^{24}$ = 1.5332.

EXAMPLE 18

30 g of a 50% (by weight) dispersion of sodium hydride in oil are washed free from oil with three portions of low-boiling petroleum ether and then added to 75 ml of absolute dimethylformamide. Within 1 hour, 12.4 g of p-hydroxybenzyl alcohol are added to the resulting mixture with stirring. Thereafter, 30 g of propargyl bromide are added dropwise over a period of 45 minutes at such a rate that the temperature does not exceed 35°–40°C. The mixture is stirred for a further 3 hours at room temperature, and then the excess sodium hydride is decomposed by treatment with water. A further 100 ml of water are added, and the mixture is extracted 3 times with diethyl ether. The ether extract is washed neutral with water, dried over sodium sulphate, filtered and evaporated. The residue is chromatographed on silica gel using methylene chloride as the elution agent. There is obtained p-α-bis-(2-propynyloxy)-toluene; $n_D^{24}$ = 1.5520.

EXAMPLE 19

25 g of a 50% (by weight) dispersion of sodium hydride in oil are washed free from oil with three portions of low-boiling petroleum ether and then added to 75 ml of absolute dimethylformamide. 12.2 g of p-methylbenzyl alcohol are added portionwise to this mixture, and the resulting mixture is stirred for 30 minutes. 11.8 g of propargyl bromide are added dropwise with stirring so that the temperature does not exceed 35°–40°C. The mixture is stirred for 3 hours at room temperature, then cooled to 5°C. in an ice-bath, and the excess sodium hydride decomposed by the addition of 25 ml of water.

The mixture is diluted with a further 100 ml of water, extracted 3 times with diethyl ether, the ether extract washed neutral with water, dried over sodium sulphate and evaporated. The residue is chromatographed on silica gel using methylene chloride as the elution agent. There is obtained p-methylbenzyl 2-propynyl ether; $n_D^{23} = 1.5141$.

EXAMPLE 20

95 g of a 50% (by weight) dispersion in oil are washed free from oil with three portions of low-boiling petroleum ether and then added to 75 ml of absolute dimethylformamide. 17.7 g of 3,4-dichlorobenzyl alcohol are added dropwise to the resulting mixture with stirring. After 30 minutes, 11.8 g of propargyl bromide are added dropwise with stirring at such a rate that the temperature does not exceed 35°–40°C. The mixture is stirred at room temperature for a further 3 hours, then cooled in an ice-bath, and the excess sodium hydride decomposed by the addition of 25 ml of water. The mixture is diluted with a further 100 ml of water, extracted three times with diethyl ether, the ether extract washed neutral with water, dried over sodium sulphate and evaporated. The residue is chromatographed on silica gel using methylene chloride as the elution agent. There is obtained 3,4-dichlorobenzyl 2-propynyl ether; $n_D^{23} = 1.5489$.

become crippled. In the case where the ratio of insect-poison to propynyl benzyl ether is 0:100 (I:P = 0:100), the $LD_{50}$ values stated refer to the propynyl benzyl ether itself (and are not based on the insect-poison).

EXAMPLE 21

Aphids

For each test, one seedling of the field bean with ca 50–100 black bean aphids is sprayed with a solution of the active ingredient(s) in acetone or an aqueous spray-wash of the active ingredient(s). The seedlings are individually placed in tubes in water. After 24 and 48 hours, the dead and surviving aphids are counted and the activity calculated in %.

Table 1

| P | \multicolumn{3}{c}{$LD_{50}$ concentration based on insect-poison APHIDS} | | | | | | |
|---|---|---|---|---|---|---|---|---|
| | Methoxychlor (I:P) | | | Malathion (I:P) | | | Allethrin (I:P) | | |
| | 1:5 | 100:0 | 0:100 | 1:5 | 100:0 | 0:100 | 1:5 | 100:0 | 0:100 |
| A | 4.5 | 3.3 | 3.0 | | | | 5.7 | 5.0 | 3.0 |
| B | 4.4 | 3.3 | 3.3 | 5.2 | 5.1 | 3.3 | 5.2 | 5.0 | 3.0 |

I = Insect-poison.
P = Propynyl benzyl ether.

EXAMPLE 22

Flies

For each test, two petri dishes are sprayed with a solution of the active ingredient(s) in acetone or an aqueous spray-wash of the active ingredient(s). The dosage for each treated surface is $10^{-5}$ g/cm$^2$ = 1 kg/ha. After 2–3 hours, 10 flies aged 4–5 days are placed in each petri dish. After 1, 3 and 24 hours, the flies which are dead or crippled are counted. The $LD_{50}$ (based on insect-poison) is calculated after 24 hours on the basis of the number of dead flies.

Table II

| P | Sevin (I:P) | | | Methoxychlor (I:P) | | | Malathion (I:P) | | | Allethrin (I:P) | | |
|---|---|---|---|---|---|---|---|---|---|---|---|---|
| | 1:5 | 100:0 | 0:100 | 1:5 | 100:0 | 0:100 | 1:5 | 100:0 | 0:100 | 1:5 | 100:0 | 0:10 |
| A | >5 | 2.5 | 3.5 | 4.6 | 3.8 | >3.5 | 5.5 | 5.1 | >3.5 | | | |
| B | >5 | 2.5 | 3.5 | 4.5 | 3.8 | 3.3 | 5.5 | 5.1 | 3.3 | 5.6 | 5.5 | 3.3 |

I = Insect-poison.
P = Propynyl benzyl ether.

The experiments described in the following examples are carried out with the following representative examples of the propynyl benzyl ethers (P) of formula I having juvenile hormone-like activity, which can be utilized in combination with an insect-poison (I) to form the active substance for an insecticide composition.

A 3,4-(methylenedioxy)-α-(2-propynyloxy)-toluene
B 3,4-dimethoxy-α-(2-propynyloxy)-toluene The results for each example are provided in a table at the end thereof. The concentration for each $LD_{50}$ determination is stated logarithmically in terms of the concentration of insect-poison (e.g. 3 = $10^{-3}$ g/cm$^3$ = 1%). Said $LD_{50}$ values define the concentration of insect-poison present at which 50% of the insects die or

EXAMPLE 23

Spider-mites

For each test, three bean leaf discs each with a 2-day infection and with 20–40 spider-mites and eggs are sprayed with a solution of the active ingredient(s) in acetone or an aqueous spray-wash of the active ingredient(s). The dosage for each treated surface is $10^{-5}$ g/cm$^2$ = 1 kg/ha. After 2 days, the discs are assessed for dead spider-mites and after 6 days for dead spider-mites and killed eggs. (Assessment scheme: from 0–5, where 0 = 0% and 5 = 100% mortality).

W = assessment based on the mortality of the spider-mites;
O = assessment based on the mortality of the eggs.

Table III

| P | LD₅₀ concentration based on insect-poison SPIDER-MITES | | | | | | | | | | | | | | | | |
|---|---|---|---|---|---|---|---|---|---|---|---|---|---|---|---|---|---|
| | Sevin (I:P) | | | | | | Methoxychlor (I:P) | | | | | | Malathion(I:P) | | Allethrin (I:P) | | |
| | 1:5 | | 100:0 | | 0:100 | | 1:5 | | 100:0 | | 0:100 | | 1:5 | 100:0:100 | 1:5 | 100:0 | 0:100 |
| | W | O | W | O | W | O | W | O | W | O | W | O | W | W | W | O | W | O |
| A | 3.1 | | <3 | | <2 | | | | | | | | | | | | | |
| B | 3.9 | 3.5 | <3 | 3 | 3.0 | 2.7 | 3.7 | 3.7 | <3 | <3 | 3.0 | 2.7 | 4.7 | <4 | 3.0 | 4.3 | 4.1 | 3.4 <3 3.0 2.7 |

I = Insect-poison.
P = Propynyl benzyl ether.

It is claimed:

1. A compound of the formula:

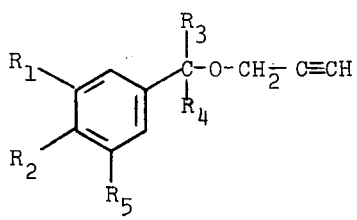

wherein $R_1$ and $R_2$ taken together form a lower alkylenedioxy group having 1 to 4 carbon atoms; $R_3$ and $R_4$ are hydrogen or lower alkyl; and $R_5$ is hydrogen or lower alkoxy.

2. The compound of claim 1 wherein said compound is 6-[(2-propynyloxy)methyl]-1,4-benzodioxane.

3. The compound of claim 1 wherein $R_3$ and $R_4$ are lower alkyl.

4. The compound of claim 3 wherein said compound is α, α-diethyl-piperonyl propargyl ether.

* * * * *

UNITED STATES PATENT AND TRADEMARK OFFICE
CERTIFICATE OF CORRECTION

PATENT NO. : 3,946,040
DATED : March 23, 1976
INVENTOR(S) : MADHUKAR SUBRAYA CHODNEKAR, ALBERT PFIFFNER, NORBERT RIGASSI, ULRICH SCHWIETER AND MILOS SUCHY It is certified that error appears in the above-identified patent and that said Letters Patent are hereby corrected as shown below:

On first page insert -

"Foreign Application Priority Data -

March 19, 1971 - Switzerland - 4121/71".

Signed and Sealed this

First Day of March 1977

[SEAL]

Attest:

RUTH C. MASON
*Attesting Officer*

C. MARSHALL DANN
*Commissioner of Patents and Trademarks*